United States Patent [19]

Wulff et al.

[11] 4,021,454

[45] May 3, 1977

[54] OLEFIN EPOXIDATION

[75] Inventors: Harald P. Wulff, Alameda, Calif.; Freddy Wattimena, Amsterdam, Netherlands

[73] Assignee: Shell Oil Company, Houston, Tex.

[22] Filed: Apr. 26, 1976

[21] Appl. No.: 680,324

Related U.S. Application Data

[63] Continuation of Ser. No. 173,326, Aug. 19, 1971, abandoned, which is a continuation-in-part of Ser. No. 812,920, April 2, 1969, abandoned.

[52] U.S. Cl. .......................................... 260/348.5 L
[51] Int. Cl.² ..................................... C07D 301/20
[58] Field of Search ............................. 260/348.5 L

[56] References Cited

UNITED STATES PATENTS

| | | | |
|---|---|---|---|
| 3,351,635 | 11/1967 | Kollar | 260/348.5 L |
| 3,391,214 | 7/1968 | Fetterly | 260/348.5 L |
| 3,505,360 | 4/1970 | Allison et al. | 260/348.5 L |

FOREIGN PATENTS OR APPLICATIONS

| | | | |
|---|---|---|---|
| 1,524,851 | 4/1968 | France | 260/348.5 L |

OTHER PUBLICATIONS

OXIDATION — Techniques and Applications in Organic Synthesis — edited by Robert L. Augustine, Chapter 3 (Epoxidation of Olefins by Hydroperoxides by Richard Hiatt) pp. 113, 124–127, 138–140.

*Primary Examiner*—Norma S. Milestone

[57] ABSTRACT

Substituted olefins are epoxidized by contacting a hydrocarbon hydroperoxide and a substituted olefin in the presence of a catalyst of an inorganic oxygen compound of silicon in chemical combination with an oxide or hydroxide of titanium.

9 Claims, No Drawings

OLEFIN EPOXIDATION

This is a continuation of application Ser. No. 173,326, filed Aug. 19, 1971, which in turn is a continuation-in-part of application Ser. No. 812,920 filed Apr. 2, 1969, both now abandoned.

BACKGROUND OF THE INVENTION

The use of organic hydroperoxides in the epoxidation of olefins is known to offer important and distinct advantages over other methods of olefin oxide production. Organic hydroperoxides are relatively inexpensive and convenient and safe to handle. In addition, organic hydroperoxides can readily be obtained and maintained in anhydrous form, thus minimizing potential olefin oxide recovery and purification problems. Also, during the epoxidation reaction, the organic hydroperoxide is converted to other valuable products.

A variety of catalysts has been employed for the reaction of olefins with hydroperoxides. One process is that of Smith, U.S. Pat. No. 2,754,325, issued July 10, 1956, wherein soluble heteropoly acids containing transition metals such as chromium, molybdenum and tungsten are employed as homogeneous catalysts for the reaction of olefins and peroxides such as organic hydroperoxides and hydrogen peroxide. More recently, U.S. Pat. No. 3,350,422 and U.S. Pat. No. 3,351,635, issued Oct. 31, 1967, and Nov. 7, 1967, respectively, to Kollar describe the use of solutions of transition metal compounds (V, Mo, W, Ti, Nb, Ta, Rc, Sc, Zr, Te and U) as homogeneous catalysts. Although sufficiently soluble compounds of these transition metals generally may be suitable as homogeneous catalysts, their commonly available insoluble compounds, especially inorganic, in general are ineffective as catalysts. For example, U.S. Pat. No. 3,350,422 discloses that epoxidation of propylene with cumene hydroperoxide employing insoluble vanadium pentoxide as catalyst results in a propylene oxide yield (6%) which is little better than that obtained with no catalyst (4%). Similarly, inorganic compounds, particularly the oxides, of the metals disclosed in U.S. Pat. No. 3,351,635, are generally ineffective as heterogeneous catalysts. For example, as the result of experimentation, it has been found that in the reaction of 1-octene with t-butylhydroperoxide, a commercial $TiO_2$ gave a 50% conversion of hydroperoxide but essentially zero selectivity to 1-octene oxide; $ZrO_2$ gave a 76.7% conversion of hydroperoxide and essentially zero selectivity to 1-octene oxide; $Ta_2O_5$ gave a 11% conversion of hydroperoxide but only a 5% selectivity to 1-octene oxide; $CrO_3$ gave a 99% conversion of hydroperoxide but only a 22% selectivity to 1-octene oxide; $WO_3$ gave an 85% conversion of hydroperoxide but only an 8% selectivity to 1-octene oxide; $Re_2O_7$ gave an essentially quantitative conversion of hydroperoxide but essentially zero selectivity to 1-octene oxide; $TeO_2$ gave a 33% conversion of hydroperoxide but only a 7% selectivity to 1-octene oxide; $SeO_2$ gave a 97% conversion of hydroperoxide but essentially a zero selectivity to 1-octene oxide and $UO_2$ gave a 55% conversion of hydroperoxide but only 5% selectivity to 1-octene oxide. It would be of advantage, however, to effect the epoxidation of olefins with insoluble catalysts in a heterogeneous system, i.e., catalyst compositions which are substantially insoluble in the reaction mixture since heterogeneous catalyst systems generally exhibit a number of operational advantages for large-scale industrial operations. For example, heterogeneous catalyst systems do not require elaborate means for separation of catalyst composition and reaction products due to the insolubility of the catalyst composition in the reaction mixture.

SUMMARY OF THE INVENTION

It has now been found that improved epoxidation of substituted olefins with organic hydroperoxides is effected with a catalyst composition of an inorganic oxygen compound of silicon and an oxide or hydroxide of titanium in chemical combination. The catalyst composition is characterized by being essentially insoluble in the epoxidation reaction mixture providing a heterogeneous system. Moreover, the catalyst composition is further characterized by producing high olefin oxide selectivity based on hydroperoxide converted although the catalyst precursors alone, e.g., $TiO_2$, produce hydroperoxide conversion but give essentially zero selectivity to olefin oxide product.

In the preferred modification of the epoxidation process, haloalkenes and hydroxyalkenes are epoxidized.

DESCRIPTION OF PREFERRED EMBODIMENTS

The Catalyst

The catalyst composition employed for the epoxidation comprises an inorganic oxygen compound of silicon in chemical combination with an oxide or hydroxide of titanium. The oxide or hydroxide of titanium is preferably combined with the oxygen compound of silicon in a high positive oxidation state, e.g., tetravalent titanium. The proportion of the oxide or hydroxide of titanium combined in the catalyst composition can be varied, but generally the catalyst composition contains, based on total catalyst composition, at least 0.1% by weight of the oxide or hydroxide of titanium with amounts from about 0.2 to about 50% by weight being preferred and amounts from about 0.2 to about 10% by weight being most preferred.

The oxygen compound of silicon is an inorganic siliceous solid containing a major proportion of silica. In general, suitable inorganic siliceous solids are further characterized by having a relatively large surface area in relation to their mass. The term used herein and one normally used in the art to express the relationship of surface area to mass is "specific surface area". Numerically, specific surface area will be expressed as square meters per gram ($m^2/g$). Generally the inorganic siliceous solid has a specific surface area of at least 1 $m^2/g$ and preferably the average specific surface area is from 25 to 800 $m^2/g$.

One class of suitable inorganic siliceous solid are synthetic, porous silica consisting of particles of amorphous silica flocculated or linked together so that they form relatively dense, close-packed masses. Representatives of such materials are silica gel and precipitated silica. These silica products are porous, in that they have numerous pores, voids or interstices throughout their structures. The preparation and properties of such porous siliceous solids are described by R. G. Iler, "The Colloid Chemistry of Silica and Silicates", Cornell University Press, New York, 1955, Chap. VI and U.S. Pat. No. 2,657,149 of R. G. Iler, issued Oct. 27, 1953. A variety of silica gels are available commercially. Commercial silica gels consisting of at least 99% silica and having specific surface area of about 25 to about 800 $m^2/g$ and pore volume of about 0.3 to 1.3 ml/g are generally suitable.

Another class of suitable inorganic siliceous solids are synthetic, silica powders consisting of particles of amorphous silica flocculated in open-packed, readily disintegrated, loosely-knit aggregates. Representatives of silica powders are fumed, pyrogenic silica obtained by the combustion of hydrogen and oxygen with silicon tetrachloride or tetrafluoride. Fumed silicas are produced commercially and are sold by various companies such as by Cabot Corporation as "Cab-O-Sil" and by Degussa as "Aerosil". Fumed silicas suitably employed as catalyst generally consist of at least 99% silica and have surface area of about 50 to about 400 m²/g and particle size of about 0.007 to about 0.05 micron.

Another class of inorganic siliceous solids are synthetic inorganic oxide materials containing a major proportion of silica. Such materials are known as refractory oxides and include silica-alumina, silica-magnesia, silica-zirconia, silica-alumina-boria and silica-alumina-magnesia.

Other suitable inorganic siliceous solids are naturally-occurring crystalline mineral silicates. Exemplary naturally-occurring mineral silicates are asbestos minerals such as serpentine (hydrous magnesium silicate); clay minerals such as hectorite (magnesium lithium silicate), kaolins and bentonites; micaceous minerals such as phlogopite (potassium magnesium aluminium silicate) and vermiculete (a hydrous magnesium silicate).

Synthetic amorphous inorganic siliceous solids are preferred over naturally-occurring crystalline mineral silicates as catalyst precursors. Particularly preferred synthetic inorganic siliceous solids are those consisting essentially of pure silica, e.g., at least 90% silica.

In certain modifications of the process, it is desirable to include within the catalyst lesser amounts of a catalyst promoter in addition to the oxygen compound of silicon and the oxide or hydroxide of titanium. Suitable catalyst promoters are the alkali metals of atomic number from 11 to 55 inclusive, i.e., sodium, potassium, rubidium and cesium, and alkaline earth metals of atomic number from 12 to 56 inclusive, i.e., magnesium, calcium, strontium and barium. The form in which the catalyst promoters are employed as preferably the oxide, although compounds which are readily converted to the oxide are also suitably employed as these are typically converted to the oxide as during pretreatment subsequent to the formation of the initially prepared catalyst composition but prior to use.

When present, the optimum amount of catalyst promoter employed depends in part upon the atomic number of the catalyst promoter. Catalyst promoters of high atomic number, e.g., barium, are generally employed in larger amounts than catalyst promoters of low atomic number, e.g., magnesium. However, the use of excessive amounts of catalyst promoter may be detrimental to catalyst selectivity. In most instances, amounts of catalyst promoter up to about 5% by weight, calculated as metal on total composition, are satisfactory. Amounts of catalyst promoters of up to 2% by weight are preferred and amounts up to about 0.5% by weight are particularly preferred.

The use of the catalyst promoter, is preferred when employing inorganic siliceous solids containing strongly acidic sites, e.g., inorganic siliceous solids having an intrinsic acidity of less than about −3. The intrinsic acidity of an inorganic siliceous solid, generally represented by the term $pK_a$, is determined by titration of an inorganic siliceous solid with an appropriate base in the presence of dye indicators, as disclosed, for example, in U.S. Pat. No. 2,868,688 of Benesi et al., issued Jan. 13, 1959.

The preparation of the catalyst is effected by a variety of techniques. In one technique, the catalyst composition is suitably prepared by calcining a mixture of an inorganic siliceous solid and titanium dioxide at elevated temperatures, e.g., 500° to 1000° C. In another technique, the catalyst composition is prepared by co-gelling a mixture of a titanium salt and a silica sol by conventional methods of preparing metal supported catalyst compositions. In still another technique, the catalyst composition is prepared by the surface reaction of silanol groups of an inorganic siliceous solid with a titanium salt by the procedure disclosed in U.S. Pat. No. 3,166,542 of Orzechowski and McKenzie, issued Jan. 19, 1965, U.S. Pat. No. 3,220,959 of Orzechowski, issued Nov. 30, 1965 or U.S. Pat. No. 3,274,120 of Aftandilian, issued Sept. 20, 1966. In yet another technique, a catalyst composition comprising a fumed, pyrogenic titania-silica is prepared by the combustion of hydrogen and oxygen with a mixture of silicon tetrahalide and titanium halide in accordance with conventional methods of preparing finely-divided fumed metal oxides and silica. Other techniques for incorporating an oxide or hydroxide of titanium on an inorganic siliceous-solid such as dry-mixing, co-precipitation, impregnation and ion-exchange are also suitably employed.

The catalyst composition is optionally, and preferably, subject to a pretreatment or activation prior to utilization in the process. The precise method of pretreatment will depend in part upon the form of chemical combination in which the components are provided, but in general the pretreatment comprises heating an initially prepared catalyst in an atmosphere of a non-reducing gas such as nitrogen, argon, carbon monoxide or oxygen-containing gas, e.g., air. One function served by this type of pretreatment operation is to convert the catalyst and catalyst promoter components into the form of hydroxides and oxides if these components are not initially provided in these forms. For example, initial catalyst components such as titanium chloride, tetrakismethylpropylaminotitanium and potassium chloride and converted to the corresponding oxide by heating in a non-reducing atmosphere. The pretreatment temperature is not critical and temperatures from about 350° to about 800° C are satisfactory. Typical pretreatment times are from about 1 to 18 hours. Subsequent to pretreatment, the titanium catalyst is employed in any convenient physical form, for example, as powder, flakes, spheres or pellets.

The catalyst composition may suitably incorporate non-interfering substances, especially those that are inert to the reactants and products. Of course, other substances that are known to catalyze the epoxidation of olefinically unsaturated compounds may also be present so long as they do not interfere with the catalytic activity of the titania/silica catalytic combination. Generally, the titania-silica combination may incorporate trace or minor amounts of the oxides or hydroxides of elements such as boron, tin, niobium, tantalum, chromium, molybdenum, tungsten, rhenium, uranium, bismuth and rare earth elements having atomic number from 57 to 71 inclusive.

The Substituted Olefinic Reactant

The process of the invention is generally applicable to the epoxidation of any substituted olefin, i.e., an organic compound having at least one aliphatic olefinically unsaturated carbon-carbon double bond and containing relative stable functional groups incorporating such atoms as oxygen, halogen and nitrogen. The substituted olefinic reactant is an acyclic, a monocyclic, a bicyclic or a polycyclic olefin and is diolefin or polyolefin. The olefinic linkages of diolefins and polyolefins are either conjugated or non-conjugated.

Among the oxygen-containing substituted-hydrocarbon olefins which are suitably epoxidized by the process of the invention are, for example, (a) unsaturated alcohols such as allyl alcohol, crotyl alcohol, oleyl alcohol and cyclohexenol; (b) unsaturated ethers such as diallyl ether, 3-vinyl-tetrahydropyran and phenyl allyl ether; (c) olefinically unsaturated carboxylic acids such as crotonic acid, oleic acid and tetrahydrobenzoic acid; (d) olefinically unsaturated esters such as ethyl methacrylate, allyl acetate, methyl 5-hexenoate and δ-lactone of 5-hydroxy-2-pentenoic acid; (e) olefinic ketones such as methyl allyl ketone, mesityl oxide and oct-1-en-5-one; (f) olefinic aldehydes such as crotonaldehyde, cinnamyl aldehyde and 1,2,5,6-tetrahydrobenzaldehyde; (g) olefinic epoxides such as 1,2-epoxy-5-hexene and (h) oxygen-containing compounds such as soy bean oil and corn oil.

Exemplary suitable halogen-containing substituted-hydrocarbon olefins are allyl chloride, allyl bromide, methallyl chloride, cyclohexenyl chloride, hexenyl iodide and dodecenyl fluoride.

Suitable nitrogen-containing substituted hydrocarbon olefins are, for example, olefinic nitriles such as 3-cyanocyclohexene and 4-cyanobutene-2; olefinic amides such as oleamide and N-methyl-oleamide; olefinic nitro compounds such as 4-nitro-1-butene and 4-nitro-7-bromo-1,2-dihydronaphthalene; lactam of 6-amino-4-hexenoic acid and allylpyrrolidone.

A preferred class of substituted olefinic reactants are hydroxyalkenes and haloalkenes from 3 to 40 carbon atoms, preferably of 3 to 20 carbon atoms. Suitable haloalkenes are those containing halogens of atomic number from 7 to 53 inclusive, i.e., fluorine, chloride, bromine and iodine. Preferred haloalkenes are normal chloro- and bromoalkenes and particularly preferred are those wherein the olefinic linkage is terminal. Preferred hydroxyalkenes are normal hydroxyalkenes and particularly preferred are those wherein the olefinic linkage is terminal.

The Hydrocarbon Hydroperoxide

The hydroperoxide reactants of the process of the invention are tertiary alkyl hydroperoxides, i.e., an alkane having a hydroperoxy group substituted on a tertiary carbon atom, or aralkyl hyroperoxides wherein the hydroperoxy group is on a carbon atom attached directly to the aromatic ring. Suitable tertiary alkyl hydroperoxides have from 4 to 20 carbon atoms and include tertiary butyl hydroperoxide, tertiary amyl hydroperoxide, tertiary hexyl hydroperoxide and tertiary octyl hydroperoxide. Suitable aralkyl hydroperoxides have from 7 to 20 carbon atoms and include primary aralkyl hydroperoxides such as benzyl hydroperoxide, secondary aralkyl hydroperoxides such as alphamethylbenzyl hydroperoxide (ethylbenzene hydroperoxide), alpha-ethylbenzyl hydroperoxide and tetralin hydroperoxide and tertiary aralkyl hydroperoxides such as alpha,alpha-dimethylbenzyl hydroperoxide, alpha,alpha-diethylbenzyl hydroperoxide and diisopropylbenzene hydroperoxide. Preferred hydroperoxides are tertiary butyl hydroperoxide and ethylbenzene hydroperoxide.

In the epoxidation reaction, the molar ratio of olefin reactant to hydroperoxide can vary over a wide range and a molar excess of either the olefin reactant or hydroperoxide of up to as high as 100:1 can be used. In general, molar ratios of olefin reactant to hydroperoxide varying from about 50:1 to about 1:10 are satisfactory, although it is preferred to employ molar ratios of olefin reactant to hydroperoxide of about 20:1 to about 1:1.

The hydroperoxide reactant may be supplied in dilute or concentrated, purified or unpurified form. Hydrocarbon hydroperoxides are economically prepared by direct oxidation as exemplified by U.S. Pat. No. 2,845,461 of Winkler et al and U.S. Pat. No. 2,867,666 of Erickson et al. In such oxidations molecular oxygen is passed through hydrocarbon to convert at least a portion of the hydrocarbon to hydroperoxide. Generally, the hydroperoxide is present in concentration of about 5 to 70% by weight in the starting hydrocarbon. Side products such as alcohols and other impurities are also often present in minor amount. This oxidation product may be suitable used without treatment although it may in some cases be preferable to concentrate or purify the hydroperoxide such as by distillation.

The Reaction Conditions

The process of the invention is conducted in the liquid phase in solvents or diluents which are liquid at reaction temperature and pressure and are substantially inert to the reactants and the products produced therefrom. Illustrative suitable solvents are oxygen-containing solvents such as fully esterified polyacyl esters of polyhydroxyalkanes, e.g., glycerol triacetate, tetraccyl esters of erythritol, diethylene glycol diacetate; monoesters such as butyl propionate and phenyl acetate; ketones such as acetone, diethyl ketone and methyl isobutyl ketone, ethers such as dibutyl ether, dioxane and tetrahydrofuran; as well as nitrogen-containing solvents such as nitriles, e.g., acetonitrile and propionitrile and dialkylamides such as dimethylformamide. Preferred solvents are mononuclear aromatics such as benzene, toluene, chlorobenzene o-dichlorobenzene; and alkanes such as octane, decane, and dodecane. Particularly preferred solvents are the hydrocarbons employed for producing hydroperoxide reactant, e.g., alkylbenzenes such as ethylbenzene and isopropylbenzene and tertiary alkanes (an alkane containing a carbon atom attached to three other carbon atoms) such as isobutane and isohexane. In certain modifications of the epoxidation process, a portion of the olefinic reactant serves as the reaction solvent and not added solvent is needed. In most instances, however, added solvent is used and amounts up to about 20 moles of solvent per mole of organic hydroperoxide are satisfactory. The process is preferably conducted in an inert reaction environment so that the presence of reactive materials such as water is desirably avoided. Suitable reaction conditions are therefore substantially anhydrous.

The epoxidation reaction is suitably conducted by any of a variety of procedures. In one modification, the entire amounts of reactants, the catalyst and the solvent are charged to an autoclave or similar pressure reactor and the reaction mixture is maintained with agitation at reaction temperature and pressure for the desired reaction period. In another modification, one reactant is added to the remaining reaction mixture components in increments, as by adding the organic hydroperoxide to a mixture of the olefinic reactant, the catalyst and the solvent maintained at reaction temperatures and pressure. In yet another modification, reaction is effected in a continuous manner as by contacting the olefin reactant, the organic hydroperoxide and the solvent during passage through a reaction zone in which the solid catalyst is maintained in particulate form. By any modification, the epoxidation process is conducted at moderate temperatures and pressures. Suitable reaction temperatures vary from about 25° to about 200° C, but preferably from 50° to 150° C. The reaction is conducted at or above atmospheric pressure. The precise pressure is not critical so long as the reaction mixture is maintained substantially in a non-gaseous phase. Typical pressures vary from about 1 to about 100 atmospheres.

At the conclusion of the reaction, the product mixture is separated and the products are recovered by conventional methods such as fractional distillation, selective extraction, filtration and the like. The reaction solvent, the catalyst and any unreacted olefin or hydroperoxide are recycled for further utilization.

The Products

According to the process of the invention the olefinic reactant is epoxidized to the corresponding olefin oxide. By way of illustration, 2,3-epoxypropyl methyl ether is produced from allyl methyl ether, 1,2-epoxy-5-benzyloxypentane is produced from 5-benzyloxypentene-1, 1,2-epoxybut-4-yl chloride is produced from 1-buten-4-yl chloride, 3,4-epoxybutyl benzyl sulfone from 3-butenyl benzyl sulfone and 1-(3,4-epoxybutyl)-4-methoxybenzene is produced from 1-(3-butenyl)-4-methoxybenzene.

In the case of diolefinic reactants, it is possible to epoxidize only one of the olefinic linkages or both. By way of illustration, chloroprene is epoxidized to 3,4-epoxy-2-chloro-1-butene and/or 1,2-epoxy-3,4-epoxy-2-chlorobutane.

According to the process of the invention the hydrocarbon hydroperoxide is converted to the corresponding alcohol. The alcohol can be recovered as a co-product of the process or reconverted to the hydroperoxide by procedures such as dehydration to olefin, hydrogenation of the olefin and oxidation to hydroperoxide, or by hydrogenolysis to hydrocarbon followed by oxidation to hydroperoxide.

EXAMPLE I

A mixture of 25 g of commercial pyrogenic silica having a surface area of 390 m²/g (Cabot Corporation grade EH-5 Cab-O-Sil) and 1700 ml of n-heptane was dried by heating at reflux in a glass reactor equipped with a Dean Stark trap (to collect water-heptane azeotrope) for a period of about 19 hours. After cooling to about 25° C a 4.68 g sample of titanium tetrachloride was added to the reactor, and the reaction mixture heated to about 97° C until about one equivalent (based on $TiCl_4$) of hydrogen chloride was evolved. The hydrogen chloride evolved was removed by a stream of dry nitrogen and passed into a scrubber containing a dilute caustic. About 10 ml of water was then added in 0.5 ml portions to initiate the evolution of additional hydrogen chloride. After a reaction time of about 16 hours at 97° C the evolution of additional hydrogen chloride stopped. The reaction mixture was evaporated under reduced pressure at elevated temperature, and the silica residue dried at about 120°/180mm. The resulting silica product contained 4% by weight of titanium.

EXAMPLE II

A variety of olefinic compounds were epoxidized with titania-silica catalysts in glass reactor under the reactions conditions tabulated in Table I. In runs 1–5 the titania-silica catalyst employed was a pyrogenic silica containing 0.3% by weight of titanium (produced by the flame hydrolysis of $SiCl_4$ and $TiCl_4$). In Runs 6 and 7, samples of the titania-silica catalyst prepared in Example I were employed.

TABLE I

| Run | Olefin | Olefin, g | Catalyst, g | Hydroperoxide g | Diluent | Temp., ° C | Reaction Time, Hr. | Hydroperoxide Conversion, % | Epoxide Selectivity, % |
|---|---|---|---|---|---|---|---|---|---|
| 1 | 4-Cyanocyclohexane | 20 | 0.5 | t-Butyl (2.3g) | — | 110 | 6 | 90 | 96.5 |
| 2 | Cyclohexen-3-ol | 5 | 2 | t-Butyl (9g) | o-Dichlorobenzene (40 ml) | 110 | 20 | 84 | 85 |
| 3 | 1,2,5,6-Tetrahydro-benzaldehyde | 50 | 1 | t-Butyl (4.5g) | — | 105 | 3 | 59 | 36 |
| 4 | Mesityl Oxide | 50 | 1 | t-Butyl (4.5g) | — | 105 | 3.5 | 68.7 | 52.6 |
| 5 | Methyl β,β''-di-methyl acrylate | 25 | 0.5 | t-butyl (4.5g) | — | 110 | 20 | 55 | 87 |
| 6 | Allyl Chloride | 18.5 | 1 | t-Butyl (4.6g) | — | 110 | 2.2 | 49 | 74 |
| 7 | Allyl Alcohol | 29 | 1 | t-Butyl (4.5g) | — | 98 | 3 | 32 | 71 |

EXAMPLE III

Four series of reactions were carried out to test titania dioxide (P-25 Aerosil, DeGussa Inc.) and silica (EH-5 Cab-O-Sil, Cabot Corporation) as catalysts for the epoxidation of allyl chloride to epichlorohydrin and allyl alcohol to glycidol using ethylbenzene hydroperoxide. Each reaction was conducted by adding 0.2 g of titanium dioxide or 0.2g of silica into each of four 20 ml. ampules. A small teflon-covered magnetic stirrer bar was added and the open ampules were dried overnight in a vacuum oven at 120° C. A solution of 7.6 g of freshly distilled allyl chloride or 5.8 g of allyl alcohol and 49.0 g of 14.1%w ethylbenzene hydroperoxide in ethylbenzene was stored overnight over Linde 4A molecular sieve. A 10.0 ml aliquot of this ethylbenzene solution was then added to each dried ampule, the ampule cooled in Dry-Ice and the neck sealed off with a torch. After warming to room temperature the ampules were suspended in a 100° C oil bath and stirred magnetically. After 4 hours, the ampules were removed from the oil bath and the contents analyzed for hydroperoxide and epoxide. The results are tabulated in Table II.

Table II

| Catalyst | Olefinic Reactant | Hydroperoxide Conversion, % | Epoxide Selectivity, % |
|---|---|---|---|
| $SiO_2$ | $CH_2=CHCH_2Cl$ | 66.2 | 0 |
| $SiO_2$ | $CH_2=CHCH_2OH$ | 87.4 | 0 |
| $TiO_2$ | $CH_2=CHCH_2Cl$ | 77.5 | 0 |
| $TiO_2$ | $CH_2=CHCH_2OH$ | 84.8 | 0 |

EXAMPLE IV

A 324 mmole sample of allyl chloride was epoxidized with 15.4 mmoles of ethylbenzene hydroperoxide (16%w in ethylbenzene) in the presence of a 4.4%w Ti on silica (EH-5 Cab-O-Sil, Cabot Corporation) by a procedure similar to that of Example II. After a reaction period of 54 minutes, analysis of the reaction mixture showed a 59% conversion of hydroperoxide and a 69% selectivity to epichlorohydrin based on converted hydroperoxide.

EXAMPLE V

The epoxidation of allyl chloride was conducted with a 3.6%w Ti/1.0%w Ca on silica gel catalyst. The catalyst composition was prepared by dissolving about 14.4 g of titanium tetrachloride and 4.0 g of calcium nitrate in absolute ethanol. The resulting solution was poured over 100 g of silica gel having a surface area of 340 $m^2/g$ and a pore volume of 1.15 cc/g. The ethanol was removed in a rotary evaporator and the resulting impregnated silica gel was calcined for 2 hours at 800° C.

The epoxidation reaction was conducted in a ⅜-inch diameter stainless steel tube charged with 30 cc of the catalyst. The tube was heated in a oil bath and a mixture of 8 moles of allyl chloride per mole of ethylbenzene hydroperoxide (33%w in ethylbenzene) was passed over the catalyst at 61 psig, 88° C at a flow rate of 1.30 LHSV. Analysis of the product collected between 2.5 and 18.5 hours on stream indicated an average hydroperoxide conversion of 44.3% and an epichlorohydrin selectivity based on converted hydroperoxide of 77%.

We claim as our invention:

1. A process of epoxidizing allyl chloride by reacting in liquid phase in inert solvent at a temperature of about 25° to 200° C, the allyl chloride with a hydrocarbon hydroperoxide selected from tertiary alkyl hydroperoxide of from 4 to 20 carbon atoms and aralkyl hydroperoxide of from 7 to 20 carbon atoms wherein the hydroperoxy group is on a carbon atom attached directly to an aromatic ring in the presence of a heterogeneous, essentially insoluble catalyst composition comprising an inorganic siliceous solid in chemical combination with at least 0.1% by weight, based on total catalyst composition, of an oxide or hydroxide of titanium.

2. The process of claim 1 wherein the inorganic siliceous solid contains at least 90% by weight of silica.

3. The process of claim 2 wherein the inorganic siliceous solid is silica gel and the molar ratio of allyl chloride to hydroperoxide is from about 20:1 to 1:1.

4. The process of claim 3 wherein the hydroperoxide is ethylbenzene hydroperoxide.

5. The process of claim 3 wherein the hydroperoxide is tertiary butyl hydroperoxide.

6. The process of claim 1 wherein the catalyst composition contains from about 0.2 to about 50% by weight of the oxide or hydroxide of titanium, based on total catalyst composition.

7. The process of claim 6 wherein the catalyst composition contains from about 0.2 to about 10% by weight of the oxide or hydroxide of titanium, based on total catalyst composition.

8. The process of claim 6 wherein the catalyst composition additionally contains up to about 5% by weight, based on the total catalyst composition, of an alkali metal or alkaline earth metal.

9. The process of claim 8 wherein the alkali metal or alkaline earth metal is present in an amount of up to 2% by weight of the total catalyst composition.

* * * * *